United States Patent [19]

Higo et al.

[11] Patent Number: 5,238,815
[45] Date of Patent: Aug. 24, 1993

[54] ENZYMATIC IMMUNOASSAY INVOLVING DETECTING FLUORESCENCE WHILE OSCILLATING MAGNETIC BEADS

[75] Inventors: Yuji Higo, Nagoya; Satoru Kamada, Kanagawa, both of Japan

[73] Assignee: Toyo Soda Manufacturing Co., Ltd., Shinnanyo, Japan

[21] Appl. No.: 885,241

[22] Filed: May 20, 1992

Related U.S. Application Data

[63] Continuation of Ser. No. 707,928, May 28, 1991, abandoned, which is a continuation of Ser. No. 342,687, Apr. 25, 1989, abandoned, which is a continuation of Ser. No. 898,946, Aug. 21, 1986, abandoned.

[30] Foreign Application Priority Data

Aug. 30, 1985 [JP] Japan .................. 60-191125

[51] Int. Cl.$^5$ .............................................. C12Q 1/42
[52] U.S. Cl. ..................... 435/7.92; 435/7.9; 435/21; 435/808; 436/526; 436/534; 436/800; 436/805
[58] Field of Search ............... 435/7.9, 7.92, 21

[56] References Cited

U.S. PATENT DOCUMENTS

| | | | |
|---|---|---|---|
| 4,297,337 | 10/1981 | Mansfield et al. | 436/526 |
| 4,604,364 | 8/1986 | Kosak | 435/7.9 |
| 4,614,713 | 9/1986 | Harnisch | 435/21 |
| 4,659,657 | 4/1987 | Harnisch | 435/21 |

FOREIGN PATENT DOCUMENTS

| | | |
|---|---|---|
| 106324 | 4/1987 | European Pat. Off. |
| 2749956 | 5/1978 | Fed. Rep. of Germany |
| 2811228 | 9/1978 | Fed. Rep. of Germany |

OTHER PUBLICATIONS

Yolken: Reviews of Infectious Diseases 4(1) pp. 35-45 and 50, (1982).
Tietz, N. W., ed, *Fundamentals of Clinical Chemistry*, W. B. Saunders Company, Philadelphia, pp. 373-375 (1970).

*Primary Examiner*—Sam Rosen
*Attorney, Agent, or Firm*—Oblon, Spivak, McClelland, Maier & Neustadt

[57] ABSTRACT

Enzymatic immunoassay for estimating the concentration of antigen or antibody comprising bringing an antigen-antibody complex, which is labelled by an enzyme and is present heterogeneously in a solution, into contact with a substrate where pH of the solution is so adjusted as to be suitable for the enzyme to be activated and also for measuring the fluorescence of the substrate, measuring the time-variation of fluorescent intensity of the substrate produced by the enzyme reaction, and estimating the concentration of the antigen or the antibody from the slope of the substantially linear portion, on a characteristic curve representing variation of the fluorescence intensity with the time.

Fluorescence is measured while magnetic beads with antigen-antibody complex attached are oscillated at a specific frequency.

2 Claims, 2 Drawing Sheets

ENZYMATIC IMMUNOASSAY INVOLVING DETECTING FLUORESCENCE WHILE OSCILLATING MAGNETIC BEADS

This application is a continuation of application Ser. No. 07/707,928, filed on May 28, 1991, which was a continuation of application Ser. No. 07/342,687, filed on Apr. 25,1989, which was a continuation of application Ser. No. 06/898,946, filed on Aug. 21, 1986, all now abandoned.

BACKGROUND OF THE INVENTION

Field of the Invention

The present invention relates to an enzymatic immunoassay by which a minute amount of biological substances can be detected and/or estimated.

As one of known immunological methods to detect and/or estimate a minute amount of biological substances, the enzymatic immunoassay is recently recognized as noteworthy and actively developed through investigations, in which an enzyme is used as a label on an antigen-antibody reaction complex. This method is an alternative to the hitherto used radio-immunoassay which is carried out using radioisotopes and requires much cares in handling.

The enzymatic immunoassay may be realized in some different manners, as taught for example in "Clinical Chemistry", Vol. 22, No. 8, 1243–1255(1976). However, in general, the procedure goes as follows. At first an antigen or an antibody is affixed to the surface of the inner wall of a cell as reaction chamber or on the surface of beads placed in the cell, the antigen or antibody is brought into an antigen-antibody reaction with a conjugate which is combined with an enzyme as label to form a complex, then a substrate is introduced in the cell which, by the activity of the enzyme, gives rise to an optically detectable change (such as in fluorescent intensity, absorbance, and emission intensity), the change is measured by an optical means such as a fluoro-photometer, and an absorbance photometer, and from the result of measurement the amount of the complex containing enzyme, or hence the amount of the antigen or antibody.

In the enzymatic immunoassay which is concerned with the determination of an amount as minute as $10^{-13}$ of biological substances in general, a relatively large error is involved in the estimation and therefore a high performance of the instrument for measurements as well as removal of error sources are ardently required.

With these points in mind, the present inventors investigated the conventional processes in general of enzymatic immunoassay and found the problems described below.

The processes in the enzymatic immunoassay are generally carried out as follows: at first, an antigen-antibody-enzyme complex is formed affixed to the inner wall of the cup as the reaction chamber, on the surface of beads placed in the cup, or on an insoluble carrier, and then the complex is brought into contact with a substrate solution to start the enzyme reaction. The enzymatic immunoassay is conducted by measuring the fluorescence intensity of the substrate after a certain period of time, either stopping the enzyme reaction with a stopping solution or not. However, in these processes, the time from the initiation of enzyme reaction to the measurement should be strictly controlled, and so-called zero point correction is needed for the fluorescence intensity of the substrate because the intensity at the starting point is not always zero but shows some dispersion. Further, in the characteristic curve expressing the increase of the fluorescence intensity at the substrate, the rate of increase in the intensity becomes gradually smaller from the initiation of the enzyme reaction, and in addition the characteristic curve varies depending on the difference in the amount of enzyme. The correlation between two curves is not linear and hence errors due to difference in the measuring time are different in magnitude and depend individually on the characteristic curves.

SUMMARY OF THE INVENTION

To solve the above-mentioned problems, an object of the present invention is to improve the accuracy and precision of measurements in the enzymatic immunoassay.

Another object of the present invention is to realize a high precision measurement without any heavier load in controlling the process and procedure.

DETAILED DESCRIPTION OF THE INVENTION

Figure 1:
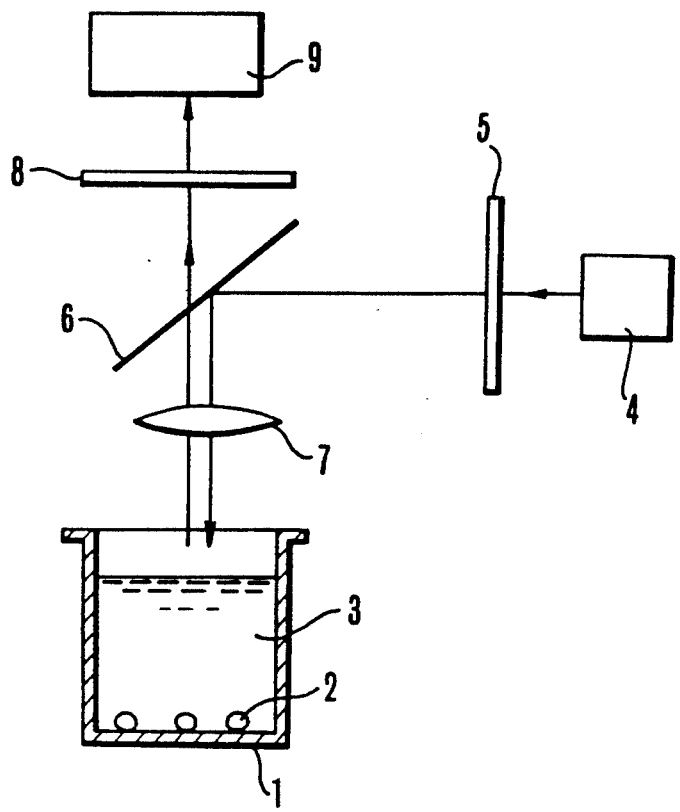
FIG. 1 is a sketch showing an example of the constitution of an apparatus to which the present invention is applied.

The characteristic features of the present invention which intends to realize the above-mentioned objects are as follows: enzymatic immunoassay for estimating the concentration of antigen or antibody comprising bringing an antigen-antibody complex, which is labelled by an enzyme and is present heterogeneously in a solution, into contact with a substrate where pH of the solution is so adjusted as to be suitable for the enzyme to be activated and also for measuring the fluorescence of the substrate, measuring the time-variation of fluorescent intensity of the substrate produced by the enzyme reaction, and estimating the concentration of the antigen or the antibody from the slope of the substantially straight linear portion on the characteristic curve representing variation of the fluorescence intensity.

The reason why the above-mentioned composition has been adopted is as follows.

The intensity of fluorescence at a substrate as a result of an enzyme reaction depends on the concentration of the substrate and the amount of enzyme (hence the amount of the antigen-antibody-enzyme complex), and directly on the amount of the enzyme when the concentration of substrate is constant. In a heterogeneous reaction where an antigen-antibody-enzyme complex is formed affixed to the surface of an insoluble carrier such as beads mentioned above and a substrate is brought into contact with the complex, observations in detail of the enzyme reaction as a variation of the fluorescence intensity reveal the substantially linear increase of the fluorescence intensity in the initial period of the enzyme reaction. In this linear region, the slope of the characteristic curve can be significantly estimated with a sufficiently small error, and the slope (or rate of increase) may linearly depend on the amount of enzyme in the solution so far as the concentration of substrate is constant. The present invention which is based on the values thus measured is adopted as useful anywhere.

The system, of which an antigen-antibody-enzyme complex can be present heterogeneously in a solution affixed on the surface of an insoluble carrier, can be an object of this invention. The insoluble carriers are exemplified by the inner wall of a vessel provided as cell, the surface of beads placed in the cell, and textiles and unwoven textiles.

The rate of increase of the fluorescence intensity that is constant in the initial linear portion gradually decreases as time goes on, as pointed out before. This is because the complex that is present heterogeneously in the solution undergoes the enzyme reaction which is rate-controlled by the diffusion of the substrate in the solution except in the initial stage of reaction. Therefore, for the purpose of expanding the interval between the two points of measurement to improve the precision in estimating the slope, it may be useful to oscillate the insoluble carrier at a low frequency to impel the reaction as diffusion-controlled. For the end, the magnetic beads placed in the cell can be oscillated by an oscillating magnetic field. The frequency is selected usually 10-180/min. preferably 70-120/min, and in case of beads they are preferably moved in an alternatingly linear or circular movement throughout the entire part of the cell bottom. Devices for these oscillation of beads may consist of a magnetically permeable cup, magnetic beads composed of magnetic (preferably paramagnetic) powder such as ferrite combined with a resin binder made from polystyrene and EVA, and a magnetic device that generates an oscillating field, for example, by a permanent magnet which is moved in alternating directions. A known process may be followed to affix an antigen or antibody to the surface of beads.

The antigens and antibodies employed in the enzymatic immunoassay of the present invention are not particularly restricted. With regard to the enzyme as label and the substrate, the only necessary condition is that the pH range for activating the enzyme and that suitable for the fluorescence of the substrate overlap to each other.

The measurement of fluorescence can be performed with a suitable optical instrument. Thus, the slope of the substantially linear portion can be measured on the observed characteristic curve of the fluorescence intensity. The result is compared with a calibration graph which is prepared beforehand, to obtain the amount of enzyme, hence the amount of the antigen or the antibody.

DESCRIPTION OF THE PREFERRED EMBODIMENTS

The embodiments of the present invention will be described below with reference to the attached drawings.

In FIG. 1, 1 is a test cup, 2 is beads placed in the cup 1 (dimension of the beads is not restricted, but preferably equal or less than half of the diameter of the cell), and an antigen-antibody-enzyme complex is formed affixed on the surface of beads by a usual process. 3 is a substrate solution, the pH of which for the measurement of fluorescence intensity is selected so as to be matched with that of activating the enzyme.

Measuring the fluorescence intensity is started by means of a fluorescence detection apparatus immediately after the addition of both beads 2 and substrate solution 3 to the test cup 1.

The fluorescence detection apparatus according to the present invention consists of light source 4, filter for exciting light 5, dichroic mirror 6, focusing lens 7, filter for fluorescent light 8 and light sensor 9. Signals detected at the light sensor 9 are transferred via an appropriate amplifier to a computation circuit (including a microcomputer, but not indicated in the drawing) to calculate a characteristic curve on variation of the fluorescence intensity as a function of time.

Figure 2:
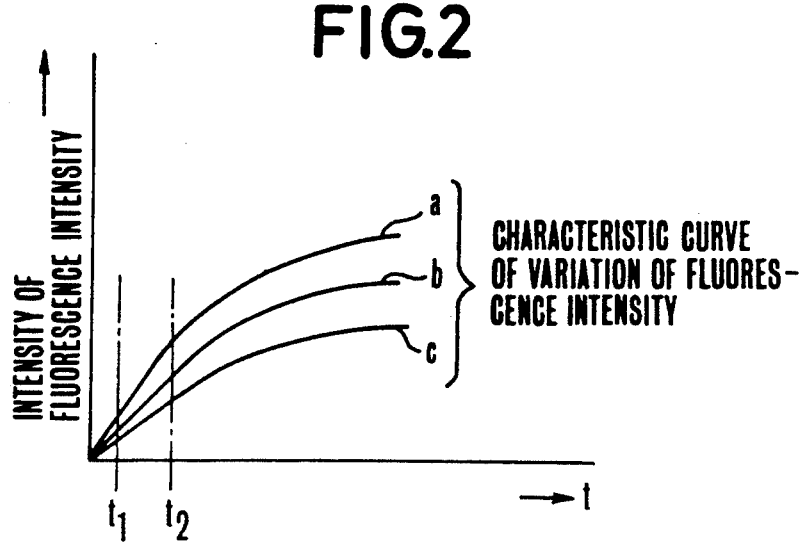
FIG. 2 shows the characteristic curves of variation of fluorescence intensity obtained by the apparatus.

In FIG. 2, a, b, and c are examples of the characteristic curve on variation of the fluorescence intensity thus obtained, showing the amounts of the antigen (or antibody) in the samples being in the order of $a > b > c$. Morever, in the early stage of the enzyme reaction, there appears a substantially linear portion in the region between t1-t2 on each curve in FIG. 2, which is hardly affected by the diffusion. Thus, if the rate of increase (or the slope) of the fluorescence intensity is determined in the above-mentioned region for each sample and compared with that of the calibration graph, determination of the amounts of the antigen or the antibody can be realized with higher accuracy and precision.

In this process the zero point correction is not required for the characteristic curves. Further, if the time interval between two measuring points is exactly controlled to estimate the rate of increase (or slope), the time for the initiation procedure of the reaction (for example, adding the substrate solution to the test cup) is not particularly required to be controlled. Thus the present invention has realized a remarkably easier and simpler procedure of measurement. This is especially advantageous for the apparatus with which many samples are to be dealt continuously, because designing engineers can have a large freedom at their disposal in deciding the time point of adding a substrate solution to the test cup, and this is invaluable in practice.

Figure 3:
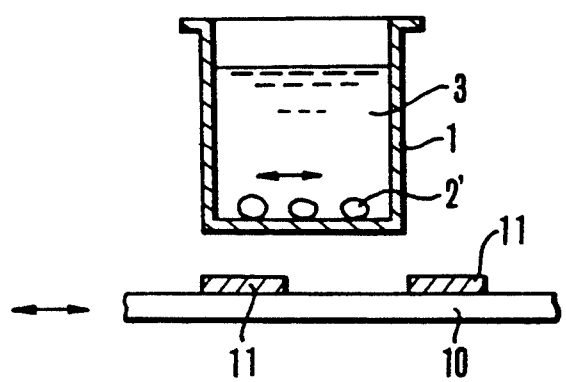
FIG. 3 explains another example of the apparatus.
Figure 4:
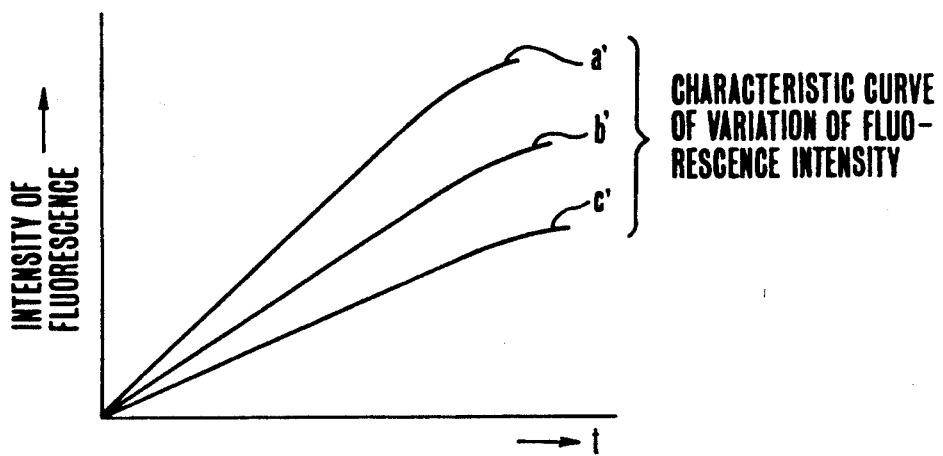
FIG. 4 is to show the characteristic curves of variation of fluorescence intensity obtained by the apparatus in FIG. 3.

In FIG. 3, beads 2' are magnetic bodies and influenced by a magnetic field and a number of permanent magnets 11 are fixed at appropriate intervals on a bar 10 that moves alternatingly closely beneath the test cup 1. In operation, the beads undergo an alternating movement in the test cup 1 in accordance with the alternatingly moving permanent magnets 11. The characteristic curves thus obtained of the variation of fluorescence intensity as a function of time, indicated as a', b' and c', contain substantially linear portions which are longer than those obtained otherwise. Therefore, the rate of increase (or slope) can be estimated with a better precision than in the example in FIG. 1, and this is markedly effective for the determination of a minute amount of biological substances.

EXAMPLE 1

Using the apparatus in FIG. 1, a complex which was labelled with an enzyme alkaliphosphatase was formed on the surface of a bead, and a substrate solution containing 4-methylumbelliferone (1 mmol/l, pH 9.5) was poured in the test cup 1 and the intensity of fluorescence was measured.

The characteristic curve obtained showing the variation of fluorescence intensity as a function of time contained a substantially linear portion from the addition of the substrate solution to the elapse of 60 sec. The slope of the curve as measured using two arbitrary points in the range was obtained with an error not more than 0.1% in a plurality of runs using the same sample.

EXAMPLE 2

Following the example in FIG. 3, the same test as in Example 1 was conducted using 10 beads of 1.4 mm in diameter which were oscillated at a frequency of 90/min.

In this case, a substantially linear portion appeared on the characteristic curve of variation of fluorescence intensity as a function of time in the range from the injection of the substrate solution to the elapse of 60 sec. The slope as measured from two points on the curve was obtained with an error not more than 0.1% in a plurality of runs using the same sample.

As has been mentioned above, the process of the present invention permits the determination of a minute amount of biological substances to be carried out with a high accuracy and precision, and further the requirements to correct the zero point offset and to strictly control the time for the procedure is either lessened or rendered irrelevant, and thus achieves great advantages. In addition, when an apparatus is assembled to treat a number of samples in a continuous manner, the present invention provides a large degree of freedom in the design of apparatus, also giving a great advantage.

What is claimed is:

1. In an enzymatic immunoassay for estimating the concentration of antigen or antibody in a sample, comprising bringing an antigen-antibody complex of said antigen and antibody, which is labelled by an enzyme into contact with a substrate which is converted into a substance emitting fluorescence by the enzyme, adjusting the pH of the solution to be suitable for the enzyme to be activated and for measuring the fluorescence of the substrate, measuring the variation as a function of time or fluorescent intensity of the substrate produced by the activation of the enzyme, the improvement comprising estimating the concentration of the antigen or the antibody from the slope of the substantially linear portion on a curve representing variation of the fluorescence intensity as a function of time, said complex being affixed to the surface of insoluble beads comprising magnetic material and the fluorescent intensity is measured while the beads are being oscillated at a frequency of 70 to 120/min, wherein said enzyme is alkaliphosphatase, said substrate is 4-methylumbeliferone, said immunoassay is free from the requirement of correcting the zero point and said immunoassay is free from the requirement of controlling the time.

2. The immunoassay of claim 1, wherein the error is less than 1%.

* * * * *